(12) United States Patent
Tanaka

(10) Patent No.: US 6,554,767 B2
(45) Date of Patent: Apr. 29, 2003

(54) ENDOSCOPIC OPTICAL ADAPTER FREELY ATTACHABLE TO AND DETACHABLE FROM ENDOSCOPE

(75) Inventor: Yasundo Tanaka, Saitama (JP)

(73) Assignee: Olympus Optical Co. Ltd., Tokyo (JP)

( * ) Notice: Subject to any disclaimer, the term of this patent is extended or adjusted under 35 U.S.C. 154(b) by 0 days.

(21) Appl. No.: 10/116,488

(22) Filed: Apr. 4, 2002

(65) Prior Publication Data

US 2002/0161284 A1 Oct. 31, 2002

(30) Foreign Application Priority Data

Apr. 4, 2001 (JP) ..................................... 2001-106174

(51) Int. Cl.[7] ............................................... A61B 1/04
(52) U.S. Cl. ...................... 600/175; 600/166; 600/170; 600/172
(58) Field of Search ................................. 600/111, 166, 600/170–173, 175, 176; 348/45, 75

(56) References Cited

U.S. PATENT DOCUMENTS

| | | | |
|---|---|---|---|
| 4,860,732 A | * | 8/1989 | Hasegawa et al. .......... 600/175 |
| 5,989,185 A | | 11/1999 | Miyazaki |
| 6,184,923 B1 | | 2/2001 | Miyazaki |
| 6,361,491 B1 | * | 3/2002 | Hasegawa et al. .......... 600/175 |

FOREIGN PATENT DOCUMENTS

| | | |
|---|---|---|
| JP | 8-201706 | 8/1996 |
| JP | 9-101465 | 4/1997 |

* cited by examiner

*Primary Examiner*—John Mulcahy
(74) *Attorney, Agent, or Firm*—Scully, Scott, Murphy & Presser

(57) ABSTRACT

An endoscopic optical adapter freely attachable to and detachable from an endoscope according to the present invention includes an adapter-side observational optical system facing an endoscope-side observational optical system provided with a solid-state image device placed in a tip constituent member of the endoscope, a unit body in which the adapter-side observational optical system is fixedly placed, an adapter body on which a first concave portion with the unit body placed therein while being free to rotate and a second concave portion with at least a part of the tip constituent member placed therein are formed, and a positioning portion which is provided in each of the adapter body and the tip constituent member and which adjusts the positional relationship between the tip constituent member and the adapter body to be a predetermined positional relationship.

8 Claims, 9 Drawing Sheets

ENDOSCOPIC OPTICAL ADAPTER FREELY ATTACHABLE TO AND DETACHABLE FROM ENDOSCOPE

This application claims benefit of Japanese Application No. 2001-106174 filed on Apr. 4, 2001, the contents of which are incorporated by this reference.

BACKGROUND OF THE INVENTION

1. Field of the Invention

The present invention relates to an endoscopic optical adapter freely attachable to and detachable from an endoscope in which a solid-state image device is placed in an endoscope-side observational optical system.

2. Description of Related Art

In recent years, endoscopes having a slender insertion portion have been used widely. These endoscopes are subjected to medical uses and industrial uses. Regarding the endoscope for the medical use, the insertion portion is inserted into a body cavity, and not only observation of organs in the body cavity, but also various therapies·treatments are performed while endo-therapy products are introduced in the body cavity through an endo-therapy product channel provided in the aforementioned insertion portion, if necessary.

On the other hand, regarding the endoscope for the industrial use, the insertion portion is inserted into boilers, the inside of tubes in machines, chemical plants or the like, the inside of engines, or the like, and observation, inspection, repair, etc., are performed.

Examples of the aforementioned endoscopes include an electronic endoscope provided with an image device such as a charge coupled device (hereafter described as CCD), at the tip portion of the insertion portion. In this electronic endoscope, an endoscope image formed on the aforementioned image device can be displayed on the screen of a monitor and, therefore, observation can be performed.

Regarding the electronic endoscope (hereafter abbreviated as endoscope) for the industrial use, hitherto, a tip optical adapter which can be fitted to the tip portion of an endoscope, while being free to attach or detach, have been publicly known. Examples of the aforementioned tip optical adapters have included, for example, those which have changed the direction of view and those for binocular observation.

In the observational optical system of an endoscopic binocular optical adapter for binocular observation, a mask provided with two openings for splitting the observation image in two is placed. The optical images passed through the two openings of this mask form images on an image pickup surface of the image device. Therefore, on the screen of the monitor, the aforementioned two openings and the observation images passed through those openings are displayed.

However, the aforementioned mask has been configured to mechanically place in the optical adapter. Consequently, regarding positional relationship, the mask may be placed while being inclined relative to a predetermined condition depending on processing precision, etc., of members constituting the optical adapter.

When the aforementioned mask is placed in a condition of being inclined, as shown in FIG. 1, each side of the opening 101, which is an observation image displayed on the screen 100 of the monitor, becomes in a condition of being inclined at an angle θ relative to each side of the screen 100.

Consequently, problems occur in quality of the observation image displayed on the screen of the monitor, and not limited to this, malfunctions may occur in observation and measurement due to occurrence of eclipse in the endoscope image when the inclination of the aforementioned mask is large.

It is an object of the present invention to provide an endoscope device capable of performing observation when an endoscope image is displayed on the screen of the monitor in the condition that endoscopic optical adapter is fitted to the endoscope, the observation image displayed on this screen becomes in a predetermined positional relationship relative to the screen, or to put it another way, for example, each side of the opening of the mask placed in the optical adapter and each side of the monitor screen are made in positional relationship of being parallel.

SUMMARY OF THE INVENTION

An endoscopic optical adapter freely attachable to and detachable from an endoscope according to the present invention is provided with an adapter-side observational optical system facing an endoscope-side observational optical system provided with a solid-state image device placed in a tip constituent member of the endoscope, a unit body in which the adapter-side observational optical system is fixedly placed, an adapter body on which a first concave portion with the unit body placed therein while being free to rotate and a second concave portion with at least a part of the tip constituent member placed therein are formed, and a positioning portion which is provided in each of the adapter body and the tip constituent member and which adjusts the positional relationship between the tip constituent member and the adapter body to be a predetermined positional relationship. Therefore, by rotating the unit body relative to the adapter body, the relative position of the adapter-side observational optical system placed in the unit body relative to the positioning portion is changed. That is, position adjustment of the adapter-side observational optical system relative to the positioning portion can be performed.

The above and other objects, features and advantages of the invention will become more clearly understood from the following description referring to the accompanying drawings.

BRIEF DESCRIPTION OF THE DRAWINGS

FIG. 2 to FIG. 8 are diagrams for explaining a first embodiment according to the present invention.

FIG. 2 is a diagram for explaining the configuration of an endoscope.

FIG. 3 is a front view of an endoscopic binocular optical adapter joined to the tip portion of an endoscope.

FIG. 4 is a sectional view of the section indicated by line 4—4 shown in FIG. 3.

FIG. 5 is a sectional view of the section indicated by line 5—5 shown in FIG. 3.

FIG. 7 is a diagram showing positional relationship between an opening of a mask and a screen of a monitor.

FIG. 8 is an enlarged diagram showing a joint portion of an endoscope and an endoscopic binocular optical adapter.

FIG. 9 and FIG. 10 are diagrams for explaining a second embodiment according to the present invention.

FIG. 9 is a diagram for explaining the configuration of a side-view type endoscopic binocular optical adapter.

DETAILED DESCRIPTION OF PREFERRED EMBODIMENTS

A first embodiment according to the present invention will be described with reference to FIG. 2 to FIG. 8.

Figure 1:
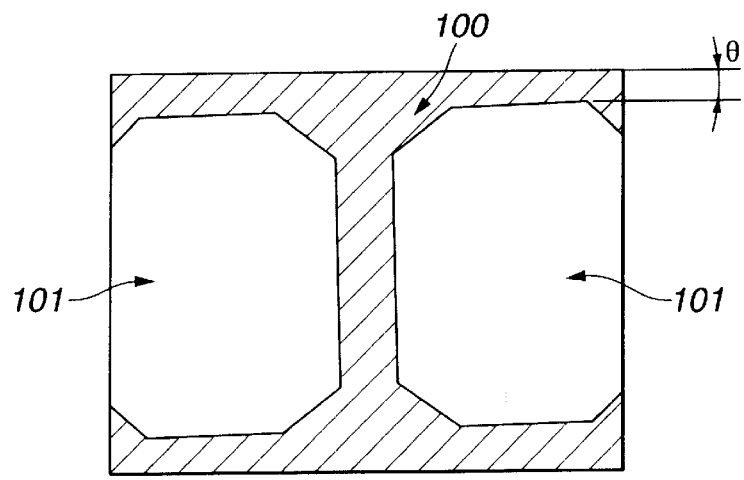
FIG. 1 is a diagram showing an example of positional relationship between an opening of a mask in an endoscopic binocular optical adapter having a conventional configuration and a screen of a monitor.
Figure 2:
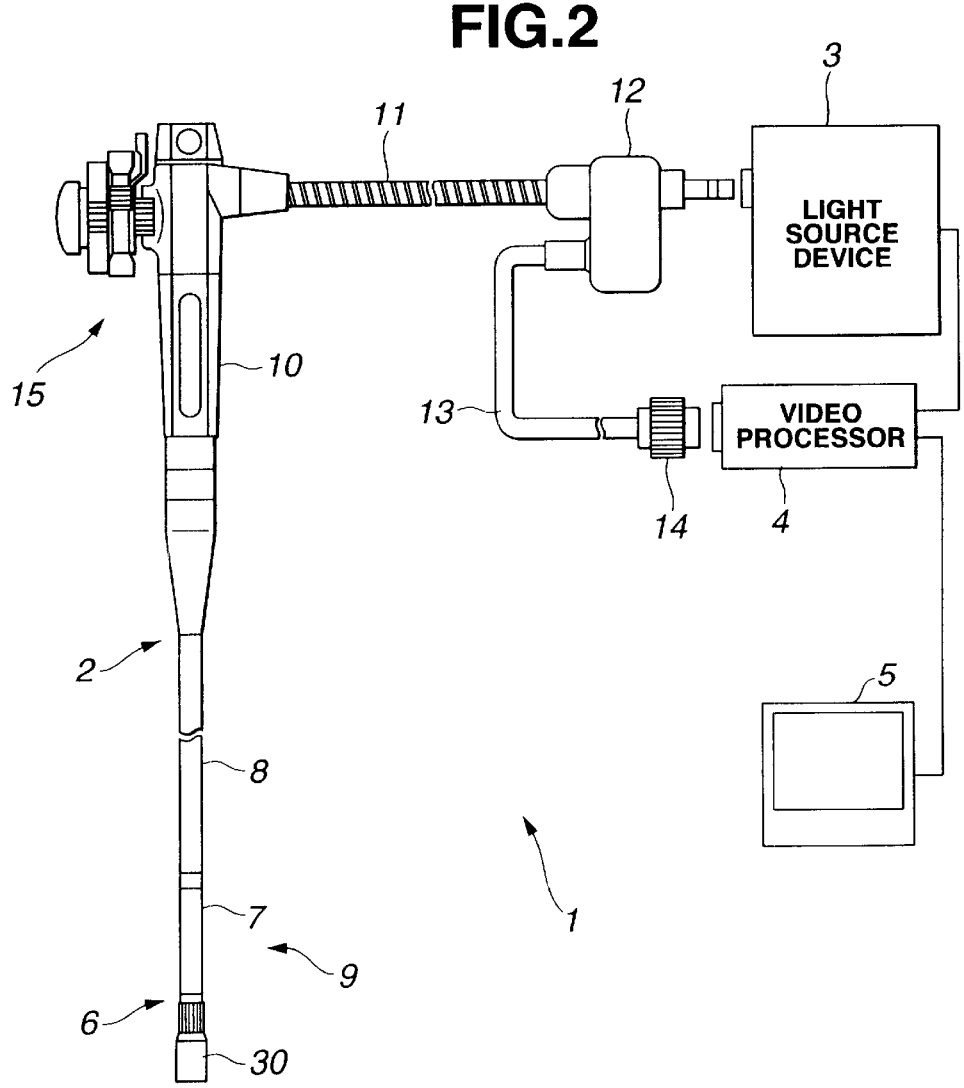

As shown in FIG. 2, an endoscope device 1 according to the present embodiment is primarily composed of an electronic endoscope (hereafter abbreviated as endoscope) 2, a light source device 3, a video processor 4, a monitor 5, an endoscopic binocular optical adapter (hereafter abbreviated as binocular adapter) 30 which is one of endoscopic optical adapters.

The aforementioned endoscope 2 includes, for example, a CCD (refer to reference numeral 23 in FIG. 5) which is a solid-state image device for producing an observation image of an inspection area. The aforementioned light source device 3 supplies illumination light to the aforementioned endoscope 2. The aforementioned video processor 4 performs control of the aforementioned endoscope 2 and signal conditioning for generating a video signal from an image signal gained by the aforementioned CCD. The aforementioned monitor 5 receives the video signal output from the aforementioned video processor 4 and displays the observation image. The aforementioned binocular adapter 30 is one of tip optical adapters fitted to the aforementioned endoscope 2 while being free to attach or detach, and a binocular mask (refer to reference numeral 32 in FIG. 4, hereafter abbreviated as mask) is placed in binocular optical system, described below, which is an observational optical system.

The aforementioned endoscope 2 includes a tip portion 6 provided with a hard tip constituent member (refer to reference numeral 26 in FIG. 5), and a slender insertion portion 9 configured by joining, for example, a curved portion 7 capable of curving upward, downward, leftward, or rightward and a flexible pliable tube portion 8 having pliability. An illuminational optical system, an observational optical system, etc., are placed at the aforementioned tip portion 6. A universal code 11 is extended from the side portion of a control portion 10 located at the base end side of the aforementioned insertion portion 9. A light guide (refer to reference numeral 21 in FIG. 5), a signal wire, etc., are inserted into this universal code 11.

A light guide connecter 12 is provided at the end portion of the aforementioned universal code 11. This light guide connecter 12 is connected to the aforementioned light source device 3 while being free to attach or detach.

An electric connector 14 connected to the aforementioned video processor 4, while being free to attach or detach, is provided at the end portion of the signal cable 13 extended from the side portion of the aforementioned light guide connecter 12.

The aforementioned tip optical adapter is freely attached to or detached from the tip portion 6 of the aforementioned endoscope 2, and this tip optical adapter includes an observational optical system having different specifications on a sort basis. Therefore, optical characteristics of an endoscopic observational optical system 20 provided in the endoscope 2 can be converted to desired characteristics by appropriately selecting and exchanging this tip optical adapter.

Incidentally, the illumination light emitted from a lamp, although not shown in the drawing, in the aforementioned light source device 3 is transmitted to the tip portion 6 of the insertion portion 9 through the light guide 21 constituting the illuminational optical system inserted through the universal code 11, the control potion 10, and the insertion portion 9. Reference numeral 15 denotes a curving control knob in order to control curving of the aforementioned curved portion 7.

The configurations of the binocular adapter 30 and the tip portion 6 of the endoscope 2 will be described with reference to FIG. 3 to FIG. 6.

The aforementioned binocular adapter 30 is composed of a binocular optical system 33 configured by placing a mask 32, a relay optical system 35 configured by a plurality of optical lenses 34 located rearward of this binocular optical system 33, a unit body 37 in which this relay optical system 35 and the aforementioned binocular optical system 33 are integrally fixed, an adapter body 38 in which this unit body 37 and the aforementioned endoscope 2 are placed, and a cover member 40 thread-engaged and fixed to this adapter body 38 with, for example, a fixing screw 39.

Figure 6A:
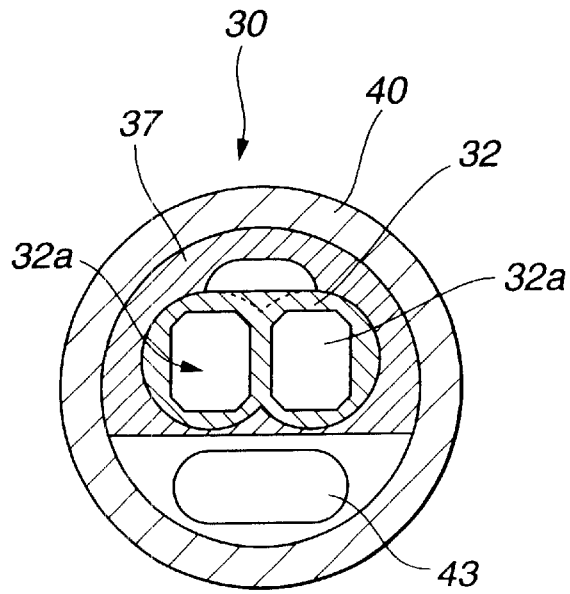
FIG. 6A is a sectional view of the section indicated by line 6A—6A shown in FIG. 5.

In the aforementioned mask 32, as shown in FIG. 6A, a pair of, for example, octagonal openings 32a are formed at a predetermined interval, and are placed among a plurality of optical lenses 31.

The aforementioned plurality of optical lenses 34 transfer optical images passed through respective openings 32a of the aforementioned mask 32.

On the aforementioned unit body 37, the aforementioned relay optical system 35 and the aforementioned binocular optical system 33 are integrally fixed so as to configure an adapter-side observational optical unit (hereafter abbreviated as adapter unit) 36 which is an adapter-side observational optical system.

A first concave portion 38a and a second concave portion 38b are formed on the aforementioned adapter body 38. The unit body 37 is placed in the aforementioned first concave portion 38a while being free to rotate. The aforementioned second concave portion 38b is a joint portion in which a convex portion (refer to reference numeral 26a in FIG. 5) of a tip constituent member 26 of the aforementioned endoscope 2 is placed.

A first optical member 41 to become an observation window and a second optical member 42 to become an illumination window are provided at the tip surface of the aforementioned cover member 40.

Figure 5:
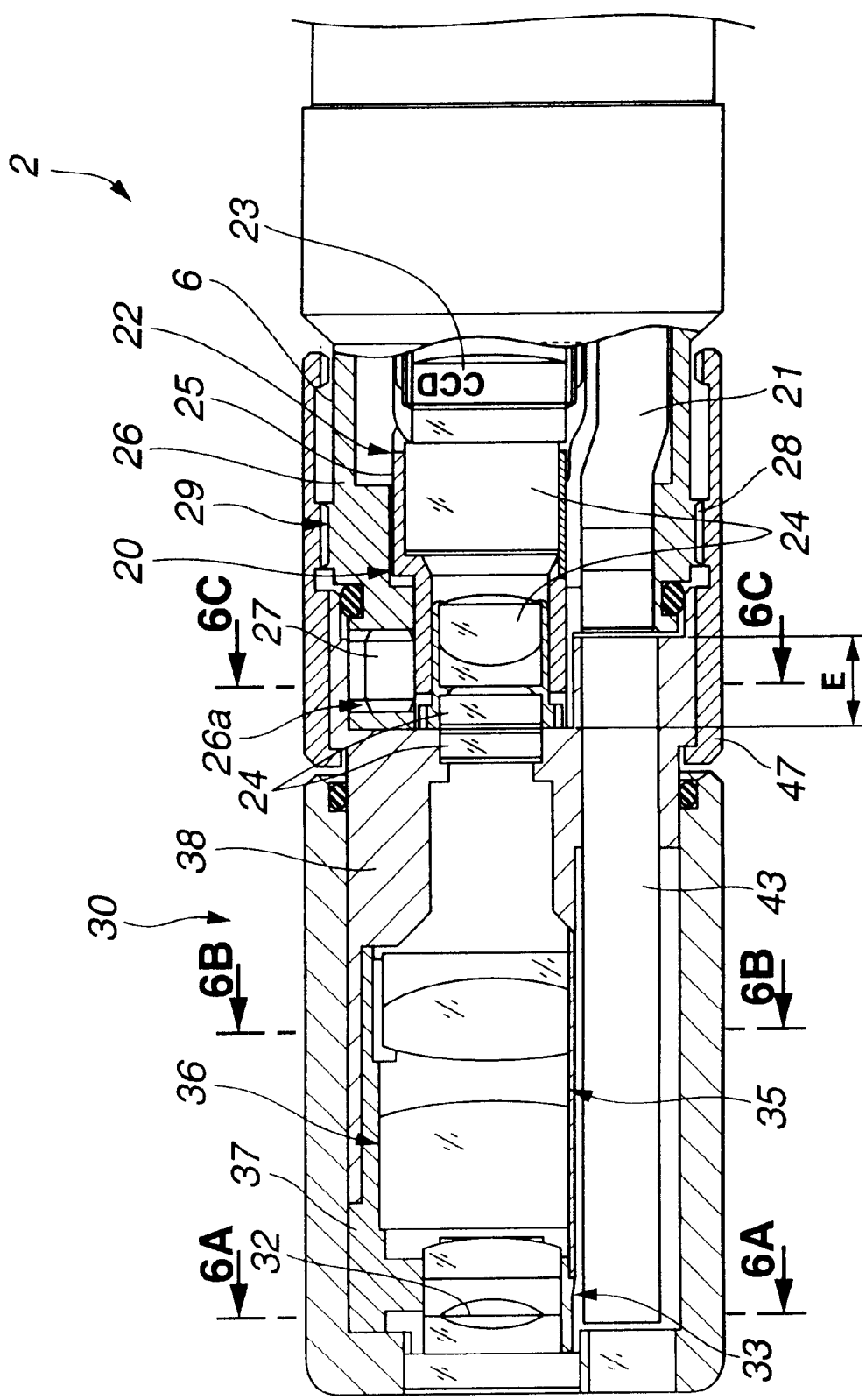

As shown in FIG. 5, one end portion of an illumination light transmission member 43 configured by being provided with the light guide or a rod lens constituting an adapter-side illuminational optical system for transmitting the illumination light is adhered and fixed to the base end portion of the aforementioned adapter body 38.

Figure 6B:
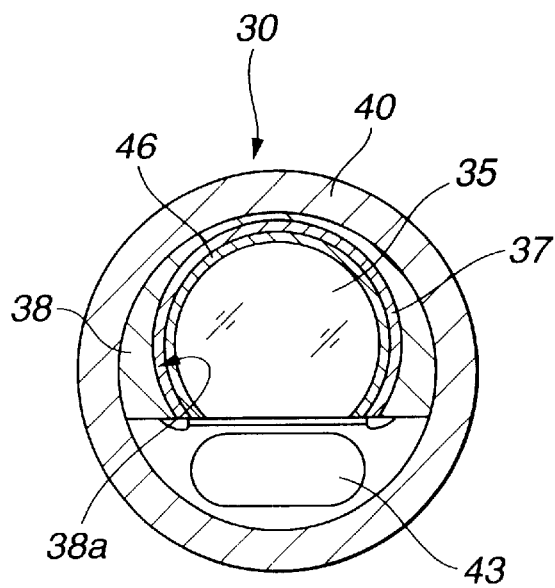
FIG. 6B is a sectional view of the section indicated by line 6B—6B shown in FIG. 5.

As shown in FIGS. 6A and 6B, the tip portion side formed into the predetermined shape of the aforementioned illumination light transmission member 43 is placed in a space portion formed by the aforementioned adapter unit 36 and the aforementioned cover member 40. At this time, regarding the positional relationship, the aforementioned illumination light transmission member 43 is adjacent to the aforementioned adapter unit 36.

Figure 3:
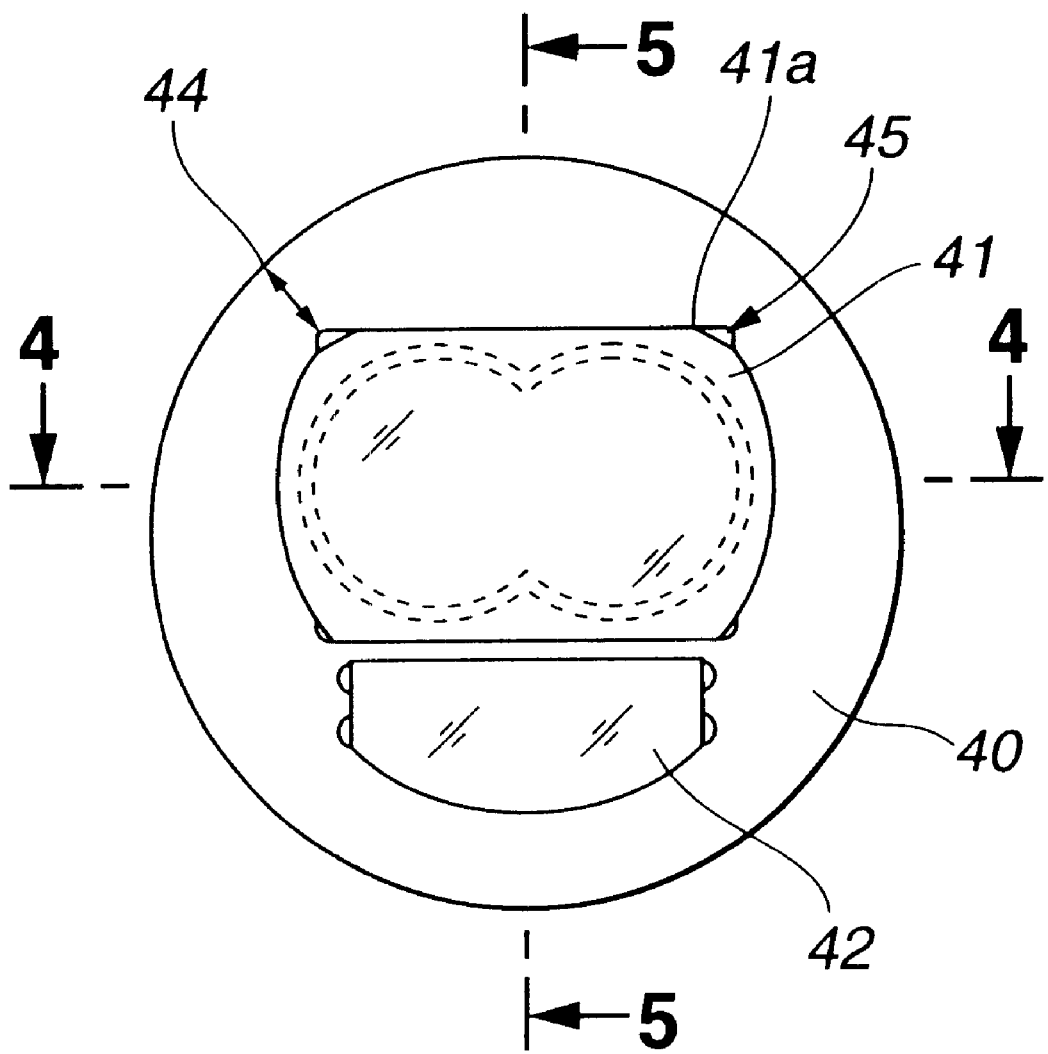

The aforementioned first optical member 41 is provided with a flank 41a at the part corresponding to a thin portion 44 of the first optical member 41, as shown in FIG. 3, in order to prevent fracture by a shock applied to the thin portion 44 of the aforementioned cover member 40. Furthermore, a recess portion 45 is also formed on the transmission hole side in which this first optical member 41 is placed. Accompanying this, when a shock is applied to the neighborhood of the thin portion 44 of the cover member 40, the shock is prevented from being transferred directly to the aforementioned first optical member 41. Therefore, this first optical member 41 is unlikely to fracture by the shock.

Figure 4:
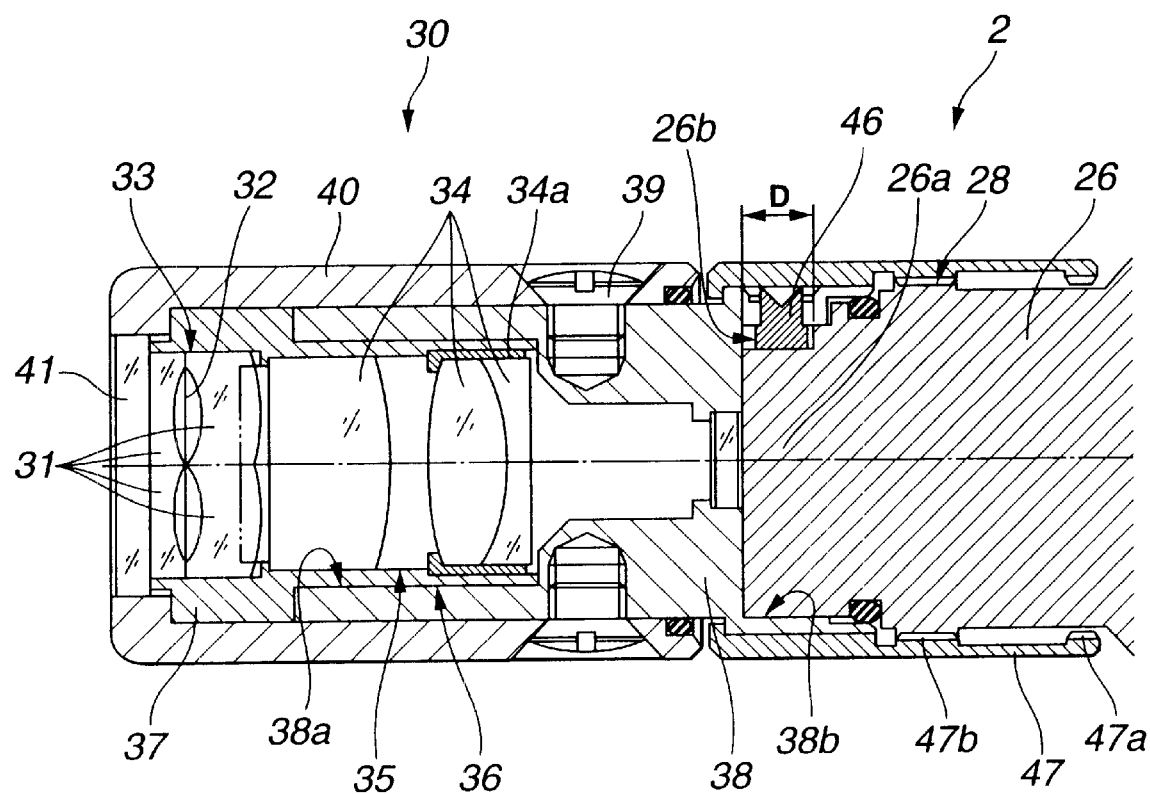

Incidentally, reference numeral 34a shown in FIG. 4 denotes a lens frame for holding the optical lenses 34 on the base end portion side constituting the aforementioned relay optical system 35. This lens frame 34a is fixed to a predetermined position at the base end portion of the aforementioned unit body 37 by adhesion.

On the other hand, as shown in FIG. 5, an image unit 22 constituting the endoscope-side observational optical system is placed at the tip portion 6 of the aforementioned endoscope 2. This image unit 22 is primarily composed of a CCD 23 which is a solid-state image device, and a plurality of optical lenses 24, ... , 24 which form an optical image on the image pickup surface of this CCD 23.

The aforementioned plurality of optical lenses 24, ... , 24 are placed in an endoscope-side lens frame 25 in which a plurality of lens frames are fixed integrally, and this endoscope-side lens frame 25 is fixed integrally to the tip constituent member 26 constituting the aforementioned tip portion 6 with, for example, a machine screw 27.

A light guide fiber 21, which is an endoscope-side illuminational optical system, is placed adjacently to the aforementioned endoscope-side observational optical system 20 in the aforementioned tip constituent member 26.

Figure 6C:
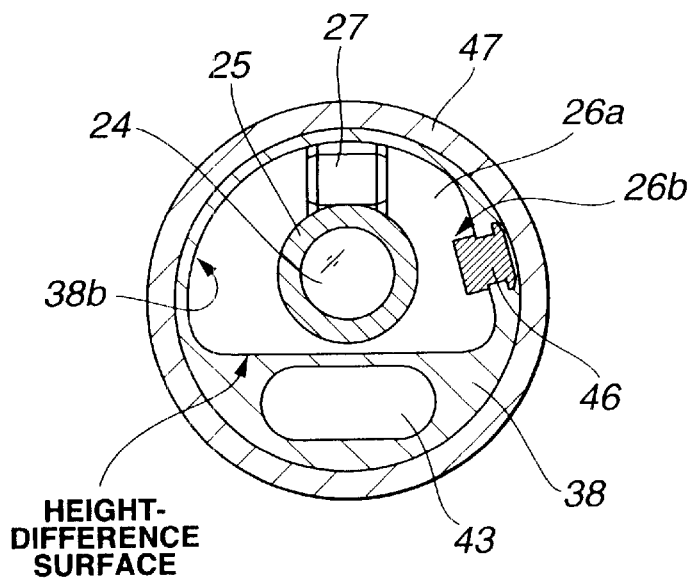
FIG. 6C is a sectional view of the section indicated by line 6C—6C shown in FIG. 5.

The part at which the endoscope-side observational optical system 20 is placed in the aforementioned tip constituent member 26 is protruded compared to the part at which the aforementioned light guide fiber 21 is placed. A convex portion 26a, which is this protruded portion, is formed into nearly the shape of a letter D as shown in FIG. 6C. An external thread portion 28 is formed at the center part of the tubular outer perimeter surface of the aforementioned tip constituent member 26.

That is, the tip side of the aforementioned tip constituent member 26 is in a stepwise shape. The aforementioned convex portion 26a is protruded by a distance E from the illumination side end surface, on which the aforementioned light guide fiber 21 is placed.

Regarding the configuration, as shown in this FIG. 5, the height-difference surface of this convex portion 26a and the height-difference surface of the adapter body 38 are in contact with each other when the aforementioned binocular adapter 30 is fitted to the endoscope 2.

As shown in the aforementioned FIG. 4 and FIG. 6C, the aforementioned convex portion 26a is inserted and placed in the second concave portion 38b formed on the base end portion side of the aforementioned adapter body 38. A positioning pin 46, which becomes a positioning portion for joining the binocular adapter 30 to a predetermined position in the aforementioned endoscope 2, is provided at a predetermined position on the inner perimeter surface of this second concave portion 38b.

This positioning pin 46 is placed in a penetration hole formed in order to communicate with the inner perimeter surface of the aforementioned second concave portion 38b by the use of a pinning tool, although not shown in the drawing. In this placement condition, the tip portion of the aforementioned positioning pin 46 is protruded toward the center axis direction by a predetermined amount.

On the other hand, a positioning groove 26b, into which the aforementioned positioning pin 46 is fitted, is formed on the tip constituent member 26 of the aforementioned endoscope 2.

That is, the aforementioned positioning groove 26b and the positioning pin 46 are in the relationship between the key groove and the key. The dimension D in the longitudinal direction of the aforementioned positioning groove 26b and the aforementioned distance E of the height difference are adjusted to be in the relationship E>D.

Consequently, when the binocular adapter 30 is joined to the endoscope 2, the height-difference surface of the adapter body 38 and the height-difference surface of this convex portion 26a become in a condition of overlapping one another before the positioning pin 46 is fitted into the positioning groove 26b.

Incidentally, the CCD 23 placed in the tip constituent member 26 of the aforementioned endoscope 2 is placed and fixed with reference to the positioning groove 26b formed in the aforementioned tip constituent member 26.

As shown in FIG. 4, FIG. 5, and FIG. 6C, the aforementioned adapter body 38 is integrally thread-engaged and fixed to the tip portion 6 of the aforementioned endoscope 2 with a setscrew member 47 formed into nearly the shape of a tube.

On the inner perimeter surface of this setscrew member 47, a first internal thread portion 47a and a second internal thread portion 47b, which are thread-engaged with the external thread portion 28 formed on the outer perimeter surface of the aforementioned tip constituent member 26, are provided at a predetermined interval.

When the aforementioned second internal thread portion 47b and the aforementioned external thread portion 28 have become in a condition of being thread-engaged, the aforementioned binocular adapter 30 and the aforementioned endoscope 2 become in a condition of being integrally joined and fixed.

Figure 8:
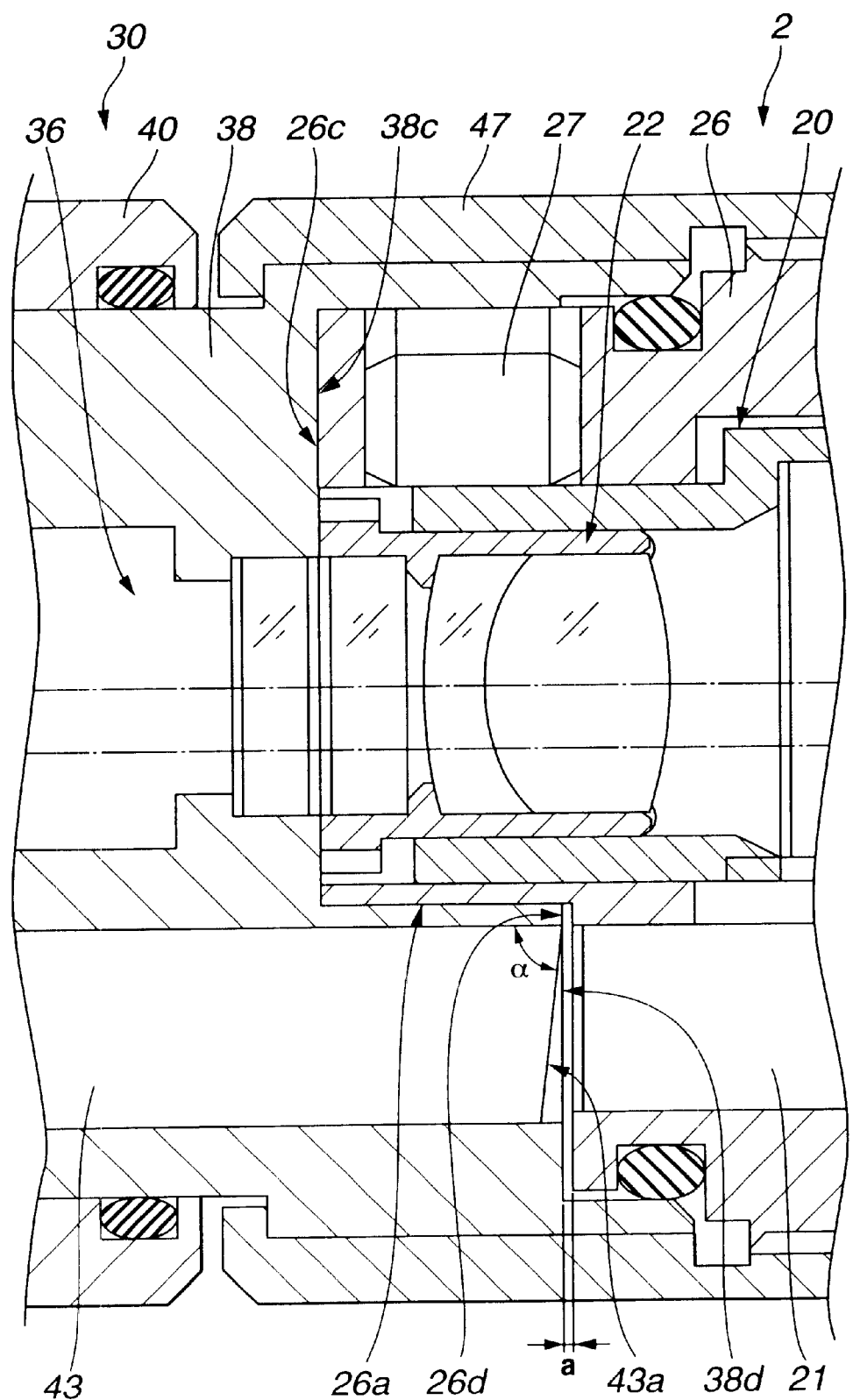

At this time, as shown in FIG. 8, an observation-side base end surface 38c of the aforementioned adapter body 38 and an observation-side tip surface 26c of the aforementioned tip constituent member 26 become in a condition of being in contact with each other and, therefore, the optical axis of the adapter unit 36 of the aforementioned binocular adapter 30 and the optical axis of the endoscope-side observational optical system 20 of the aforementioned endoscope 2 correspond with each other.

On the other hand, an illumination-side base end surface 38d of the aforementioned adapter body 38 and a illumination-side tip surface 26d of the aforementioned tip constituent member 26 are placed in a condition in which a small gap indicated by dimension a in the drawing is formed. At this time, the optical axis of the light guide fiber 21 of the aforementioned endoscope-side illuminational optical system and the optical axis of the illumination light transmission member 43 of the aforementioned adapter-side illuminational optical system correspond with each other.

As described above, by contacting the observation-side base end surface 38c and the observation-side tip surface 26c with each other without contact of the illumination-side base end surface 38d and the illumination-side tip surface 26d, degradation of optical characteristics of the observational optical system can be prevented.

Incidentally, the base end surface 43a facing the aforementioned light guide fiber 21 of the aforementioned illumination light transmission member 43 is an inclined surface indicated by an angle α in the drawing.

This inclined surface is to make the luminous intensity distribution of the illumination light transmitted through the aforementioned light guide fiber 21 in a uniform state. That is, the illumination light, which is made to exit from the tip of the aforementioned light guide fiber 21 and which is in a nonuniform state, is scattered and is made to enter the inclined surface and, in addition, the incident illumination light is irregularly reflected by the illumination light transmission member 43. Consequently, the light for illuminating an observation area in a nonuniform state is improved to uniform illumination light.

The angle α of the inclined surface is formed in order that the distance from the tip surface of the aforementioned light guide fiber 21 is increased as the distance from the optical axis of the endoscopic observational optical system is increased. Accompanying this, variations in the luminous intensity distribution caused by the illuminational optical system being offset relative to the observational optical system can be eliminated. This angle α of the inclined surface varies depending on the optical characteristics or the like of the illumination light transmission member 43.

Furthermore, the gap of dimension a is provided between the illumination-side base end surface 38d of the aforementioned adapter body 38 and the illumination-side tip surface 26d of the aforementioned tip constituent member 26 and, as a result, the illumination light made to exit from the light guide fiber 21 leaks to the outside. However, since the observation-side tip surface 26c is protruded compared to the illumination-side tip surface 26d, the illumination light having leaked to the outside is prevented from going around and entering the endoscopic observational optical system. Consequently, occurrence of flare, etc., due to the illumination light having leaked can be prevented.

Herein, an assembly process of the aforementioned binocular adapter 30 will be described.

Firstly, the optical lenses 31, the mask 32, and the optical lenses 31 are dropped through the tip-side opening of the unit body 37. Adhesion and fixing is performed and, therefore, the binocular optical system 33 is configured. On the other hand, the optical lens 34 and the optical lenses 34 held by the lens frame 34a are dropped through the base end-side opening, and are adhered and fixed. Consequently, the relay optical system 35 is configured. Therefore, the binocular optical system 33 and the relay optical system 35 are formed integrally in the adapter unit 36.

Incidentally, in order to protrude the aforementioned positioning pin 46 at a predetermined position in the second concave portion 38b of the adapter body 38, the aforementioned positioning pin 46 is, for example, swaged and fixed into the penetration hole by the use of the aforementioned pinning tool.

Subsequently, the illumination light transmission member 43 is adhered to the adapter body 38. This adapter body 38 is fitted to an optical adapter assembly fixture (hereafter, abbreviated as assembly fixture), although not shown in the drawing.

The CCD for forming an image of the mask 32 of the aforementioned binocular optical system 33 is placed on this assembly fixture. This CCD is provided with a positioning groove similar to that in the tip constituent member 26 of the aforementioned endoscope 2, and is positioned and fixed with reference to this positioning groove.

Therefore, the adapter body 38 is joined to the assembly fixture in a condition in which the positioning pin 46 of this adapter body 38 is fitted into the positioning groove of the assembly fixture.

Subsequently, the aforementioned unit body 37, in which a predetermined part on the outer surface of the relay optical system 35 side is coated with an adhesive, is dropped into the first concave portion 38a of the adapter body 38 joined to this assembly fixture. An image formed by the CCD provided on this assembly fixture is displayed on the monitor screen, and the positional relationship between the screen and the opening of the mask 32 is ascertained.

Figure 7:
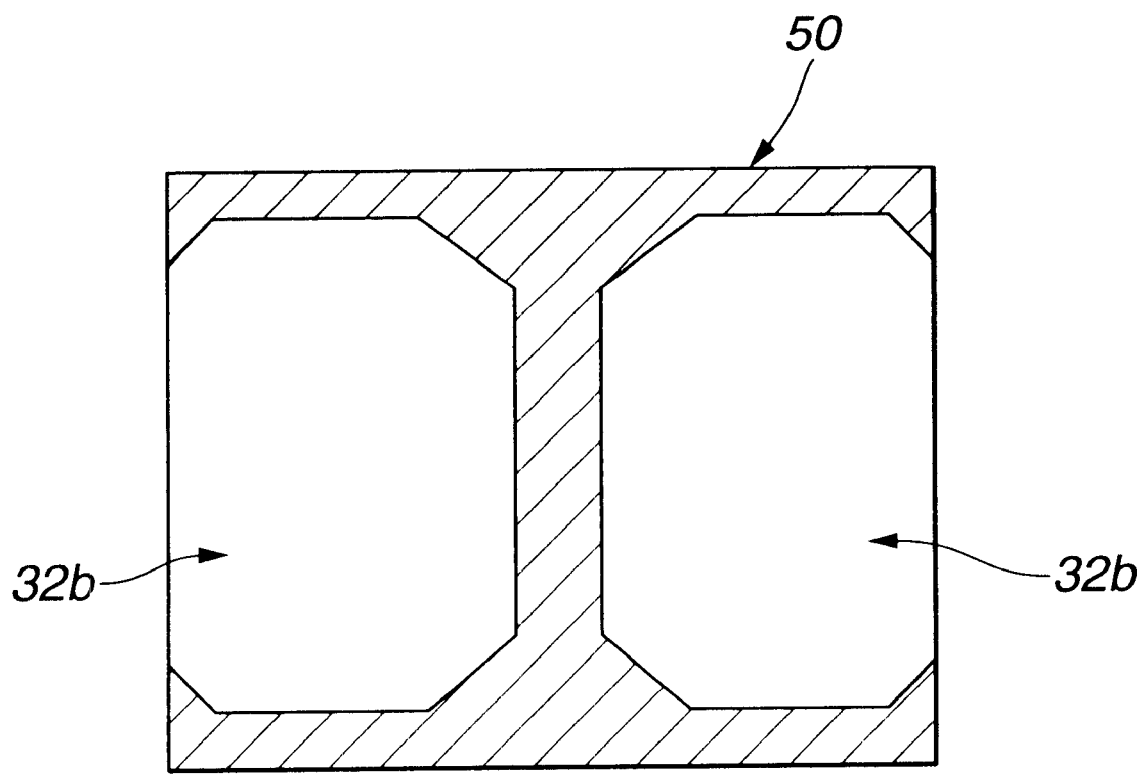

Herein, when there is a problem in the positional relationship between the screen and the opening of the mask 32, position adjustment is performed by rotating the adapter unit 36 relative to the adapter body 38 in order that regarding the positional relationship, each side of the opening images 32b of the mask 32 and each side of the monitor screen 50 become parallel, as shown in FIG. 7.

After the positional relationship between the opening images 32b of the mask 32 and the monitor screen 50 is adjusted to be parallel, that condition is maintained, and the adhesive is hardened.

Thereafter, the setscrew member 47 and the cover member 40 are inserted and placed, in that order from the tip side of the adapter body 38 integrated with the adapter unit 36, and this cover member 40 is thread-engaged and fixed to the adapter body 38 with the fixing screw 39. Consequently, the binocular adapter 30 is formed.

The joining operation of the aforementioned binocular adapter 30 to the tip constituent member 26 of the endoscope 2 will be described.

Firstly, the first internal thread portion 47a of the freely rotatable setscrew member 47 of the binocular adapter 30 is thread-engaged with the external thread portion 28 of the tip constituent member 26 of the aforementioned endoscope 2. Consequently, the binocular adapter 30 is fitted to the tip constituent member 26 from the tip side to the base end side.

When the aforementioned first internal thread portion 47a passes the aforementioned external thread portion 28, this binocular adapter 30 becomes free to move in the longitudinal direction relative to the tip constituent member 26.

Secondly, the binocular adapter 30 is moved toward the base end side of the tip constituent member 26. At this time, since the relationship between the distance E and the dimension D has been adjusted to be E>D, the height-difference surface of the tip constituent member 26 and the height-difference surface of the adapter body 38 become in a condition of overlapping one another. This condition of overlapping one another is maintained, and the aforementioned binocular adapter 30 is moved toward the base end side of the tip constituent member 26. Then, the second internal thread portion 47b is contacted with the aforementioned external thread portion 28. At this time, the second internal thread portion 47b is thread-engaged with the external thread portion 28.

The setscrew member 47 is further rotated and is moved toward the base end side and, therefore, the positioning pin 46 is fitted into the positioning groove 26b. Herein, by further rotating the aforementioned setscrew member 47, the observation-side base end surface 38c of the aforementioned adapter body 38 and the observation-side tip surface 26c of the aforementioned tip constituent member 26 become in contact with each other and, therefore, the joining of the binocular adapter 30 to the endoscope 2 is completed.

At this time, as described above, the illumination-side base end surface 38d of the adapter body 38 and the illumination-side tip surface 26d of the aforementioned tip constituent member 26 are in a condition in which the small gap a is formed therebetween.

After the joining is completed, the illumination light is supplied and observation is started. Then, on the screen of the monitor 5, an endoscope image is displayed, in which the positional relationship between the opening images 32b of the mask 32 and the monitor screen 50 becomes parallel, as shown in the aforementioned FIG. 7.

As described above, in the present embodiment, the adapter-side observational optical unit formed by providing the binocular optical system and the relay optical system in the unit body is placed in the adapter body while being free to rotate and, therefore, the endoscopic optical adapter is configured. Consequently, the position of the binocular optical system provided in the unit body can be easily adjusted in a desired positional relationship relative to the adapter body by rotating the adapter-side observational optical unit relative to the adapter body.

The positioning pin is provided in the adapter body constituting the endoscopic optical adapter while the positioning groove is provided in the tip constituent member of the endoscope. Accompanying this, since the endoscopic optical adapter is joined to the endoscope by fitting the positioning pin into this positioning groove, the positional relationship between the endoscopic optical adapter and the endoscope can be adjusted in the predetermined positional relationship.

Furthermore, the endoscope and the CCD provided in the optical adapter assembly fixture are positioned and fixed with reference to the positioning grooves formed at the predetermined position in the endoscope and the optical adapter assembly fixture as reference surfaces. Consequently, when the endoscopic optical adapter is joined to the endoscope, the positional relationship between the observational optical system of the endoscopic optical adapter and the CCD of the endoscope can be adjusted in the optimum positional relationship.

Incidentally, in the present embodiment, although the observational optical system provided in the unit body is specified to be the binocular optical system in which the mask with a pair of openings being formed therein is placed, the observational optical system is not limited to the binocular optical system. That is, it may be an observational optical system, etc., in which, for example, a polarizing filter is placed while being in need of the positional relationship relative to the CCD.

The endoscopic optical adapter is not limited to of direct-view type, and may be of side-view type as described below.

A second embodiment according to the present invention will be described with reference to FIG. 9 and FIG. 10.

The endoscopic binocular optical adapter according to the present embodiment is a side-view type endoscopic binocular optical adapter 60 in which the direction of view of the endoscope is changed to be of side-view type. The same members as those in the aforementioned binocular adapter 30 are indicated by the same reference numerals and explanations thereof are omitted.

Figure 9:
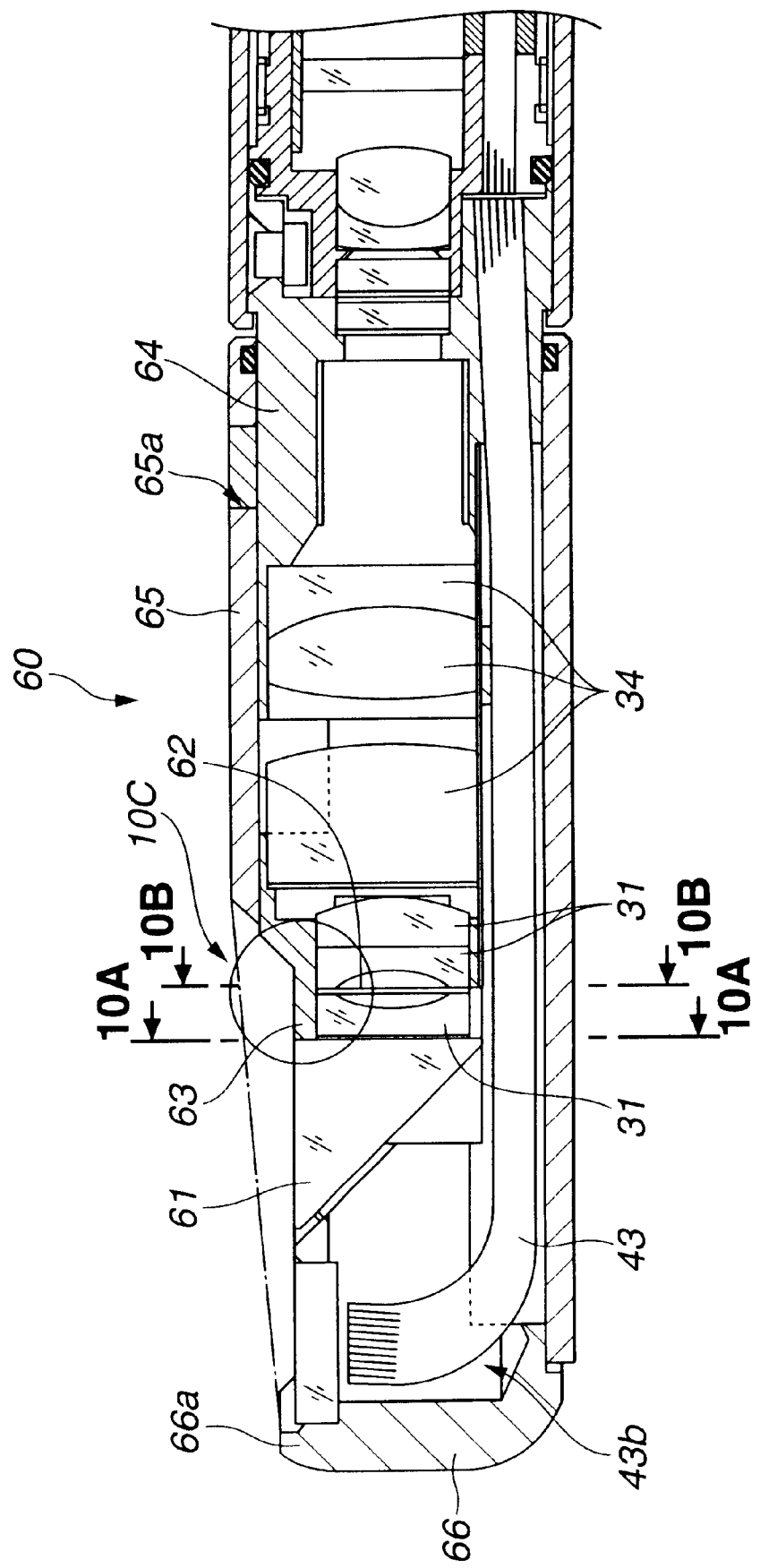
Figure 10A:
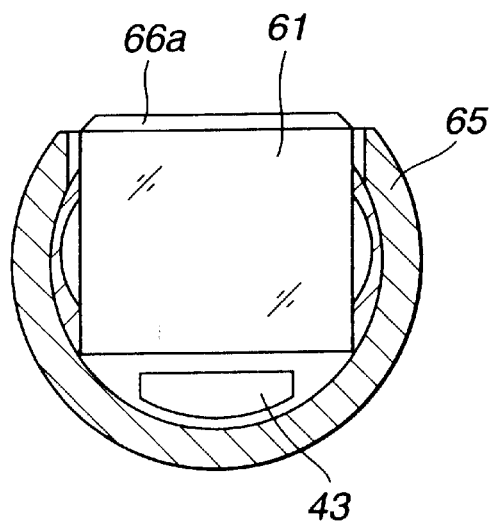
FIG. 10A is a sectional view of the section indicated by line 10A—10A shown in FIG. 9.

As shown in FIG. 9, the side-view type endoscopic binocular optical adapter (hereafter abbreviated as side-view adapter) 60 according to the present embodiment is the one in which a prism 61 is integrally configured with the configuration of the aforementioned binocular adapter 30.

Figure 10B:
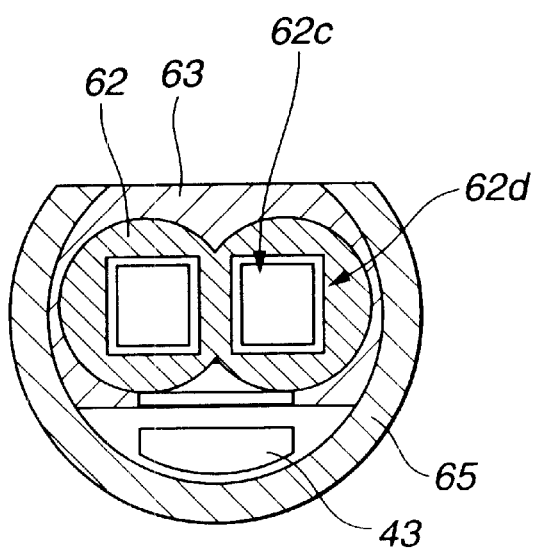
FIG. 10B is a sectional view of the section indicated by line 10B—10B shown in FIG. 9.
Figure 10C:
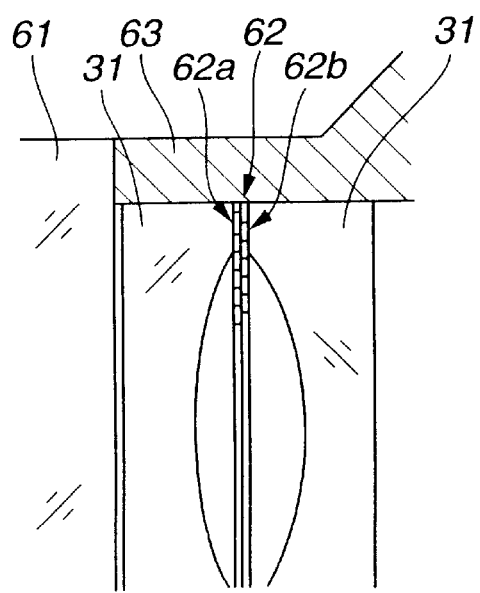
FIG. 10C is an enlarged diagram of the part indicated by an arrow 10C in FIG. 9.

As shown in FIG. 10B and FIG. 10C, the aforementioned prism 61 is integrally fixed to the front surface of the optical lenses 31 placed at the tip side of the mask 62.

The unit body 63, in which the prism 61 is placed at the tip, and the optical lens 34 is placed at the base end, and the adapter body 64, in which the optical lenses 34 are placed at the tip portion, are placed in the internal hole of a tubular outer sheath member 65. Incidentally, the base end surface of the unit body 63 covering the aforementioned optical lens 34 placed in the internal hole of the outer sheath member 65 and the tip surface of the adapter body 64 are in contact with each other.

The aforementioned adapter body 64 is integrally adhered and fixed to the outer sheath member 65 with an adhesive. The aforementioned adhesive is injected through an adhesion hole 65a formed on the internal hole of the aforementioned outer sheath member 65. Incidentally, the unit body 63 is placed while being free to rotate relative to the outer sheath member 65.

That is, the unit body 63 is free to rotate relative to the adapter body 64 in a manner similar to that in the aforementioned embodiment. The position adjustment of the mask 62 placed in the binocular optical system can be performed by rotating this unit body 63 relative to the outer sheath member 65.

Accompanying this, on the screen of the monitor, an endoscope image is displayed, in which the positional relationship between each side of the opening images of the mask 62 and each side of the monitor screen is parallel. Other actions·effects are similar to those in the aforementioned embodiment.

Incidentally, in the present embodiment, a protrusion portion 66a protruding by a predetermined amount is provided at a predetermined position of the cover member 66 in order to prevent occurrence of fracture, etc., brought about on the ground that when the position adjustment is performed by rotating the unit body 63, the prism 61 rotated is inclined, and becomes in a condition of protruding from the outside shape of a side-view adapter 60.

Accompanying this, the prism 61 is prevented from becoming in a condition of protruding from the straight line indicated by alternate long and short dashed lines bonding this protrusion portion 66a and the outer sheath member tip.

As shown in FIG. 10C, the mask 62 is formed from a plurality of thin plate members 62a and 62b in this side-view adapter 60. Consequently, the mask 62 is imparted with a function as a spacer for adjusting the interval among the optical lenses 31 to be predetermined dimensions while occurrence of flare is prevented by reflecting the incident light at the side surface of the opening of this mask 62. That is, as shown in FIG. 10B, a pair of predetermined openings 62c are formed on the thin plate member 62a provided at the tip side, and openings 62d of the thin plate member 62b provided at the base end surface side thereof are formed while being escaped by a large degree compared to the openings 62c of the aforementioned thin plate member 62a.

Furthermore, in the illumination light transmission member 43 according to the present embodiment, since a bend portion 43b is formed at an intermediate part, blank areas and luminous intensity distribution of the illumination light are improved in this bend portion 43b. Consequently, no inclined surface is formed at the end surface of the illumination light transmission member 43 facing the light guide fiber 21.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscopic optical adapter freely attachable to and detachable from an endoscope, comprising:
    an adapter-side observational optical system facing an endoscope-side observational optical system provided with a solid-state image device placed in a tip constituent member of the endoscope;
    a unit body in which the adapter-side observational optical system is fixedly placed;
    an adapter body on which a first concave portion with the unit body placed therein while being free to rotate and a second concave portion with at least a part of the tip constituent member placed therein are formed; and
    a positioning portion which is provided in each of the adapter body and the tip constituent member and which adjusts the positional relationship between the tip constituent member and the adapter body to be a predetermined positional relationship.

2. The endoscopic optical adapter according to claim 1 wherein:
    a positioning pin is provided as the positioning portion in the unit body, and a positioning groove, into which the positioning pin is fitted, is provided as the positioning portion in the tip constituent member.

3. The endoscopic optical adapter according to claim 2 wherein:
    the adapter-side observational optical unit is adjusted and placed with reference to the positioning pin by rotating the adapter-side observational optical unit relative to the adapter body, and the solid-state image device is placed with reference to the positioning groove of the tip constituent member.

4. The endoscopic optical adapter according to claim 1 wherein:
    a binocular optical system and a relay optical system are placed in the unit body so as to configure an adapter-side observational optical unit, and the adapter-side observational optical unit is free to rotate relative to the adapter body.

5. The endoscopic optical adapter according to claim 4 wherein:
    the adapter-side observational optical system is a binocular optical system provided with a mask having two openings or is an observational optical system having a change filter, which needs position adjustment relative to an image pickup surface of the solid-state image device.

6. The endoscopic optical adapter according to claim 5 wherein:
    a prism is placed in the adapter-side observational optical system in order to respond side-view observation.

7. An endoscopic optical adapter freely attachable to and detachable from a endoscope, comprising:
    an adapter-side observational optical system facing an endoscope-side observational optical system provided with a solid-state image device placed in a tip constituent member of the endoscope;
    an adapter-side illuminational optical system facing endoscope-side illuminational optical system provided in the tip constituent member;
    a unit body in which the adapter-side observational optical system is fixedly placed;
    an adapter body on which a hole potion with the adapter-side illuminational optical system placed therein, a first concave portion with the unit body placed therein while being free to rotate, and a second concave portion with at least a part of the tip constituent member placed therein are formed;
    a positioning portion which is provided in each of the adapter body and the tip constituent member and which adjusts the positional relationship between the tip constituent member and the adapter body to be a predetermined positional relationship; and
    a cover member which is placed covering the unit body and the adapter body, which forms a space for placing the adapter-side illuminational optical system, and which is provided with a first optical member and a second optical member facing the adapter-side observational optical system and the adapter-side illuminational optical system.

8. The endoscopic optical adapter according to claim 7, wherein:
    when the unit body is fitted to the tip constituent member, the observational optical system-side base end surface of the adapter body and the observational optical system-side tip surface of the tip constituent member are in intimate contact with each other while a gap having a predetermined dimension is formed between the illuminational optical system-side base end surface of the adapter body and the illuminational optical system-side tip surface of the tip constituent member.

* * * * *